Figure 1:
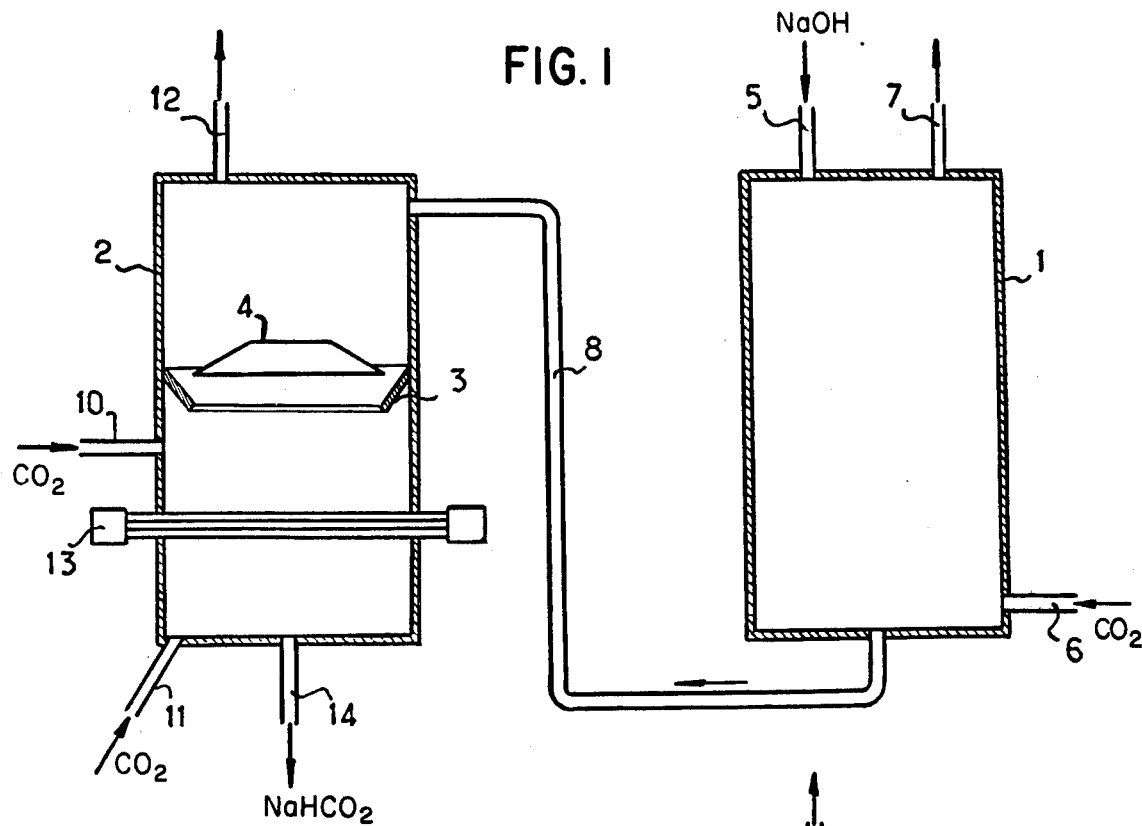

United States Patent [19]

Artur et al.

[11] 4,032,616
[45] June 28, 1977

[54] PROCESS FOR THE PRODUCTION OF SODIUM BICARBONATE FROM DIAPHRAM CELL LIQUORS

[75] Inventors: Andre Artur; Charles Meniere, both of Laneuveville Devant Nancy, France

[73] Assignee: Rhone-Poulenc Industries, Paris, France

[22] Filed: May 13, 1975

[21] Appl. No.: 577,120

[30] Foreign Application Priority Data

May 22, 1974 France ................. 74.17783
Feb. 28, 1975 France ................. 75.06290

[52] U.S. Cl. ................. 423/190; 423/422
[51] Int. Cl.² ................. C01D 7/07
[58] Field of Search ......... 423/180, 189, 190, 422, 423/424

[56] References Cited
UNITED STATES PATENTS

| | | | |
|---|---|---|---|
| 1,865,833 | 7/1932 | Chesney | 423/189 |
| 2,792,283 | 5/1957 | Hill et al. | 423/189 |
| 2,926,995 | 3/1960 | Mod el al. | 423/190 |
| 3,751,560 | 8/1973 | Neumann | 423/422 |
| 3,843,768 | 10/1974 | Neumann | 423/190 |

FOREIGN PATENTS OR APPLICATIONS 1,207,238  9/1970  United Kingdom ............... 423/422

*Primary Examiner*—O. R. Vertiz
*Assistant Examiner*—Gary P. Straub
*Attorney, Agent, or Firm*—McDougall, Hersh & Scott

[57] ABSTRACT

Process and apparatus for producing bicarbonates by converting sodium hydroxide to sodium carbonate and reacting the sodium carbonate with carbon dioxide in a gas-liquid exchange and solid discharge zone and then in a gas-liquid exchange and solid discharge zone with cooling means, with possible recirculation, whereby bicarbonate is formed and precipitated in the first zone and bicarbonate formation is completed and precipitated in the second zone.

8 Claims, 3 Drawing Figures

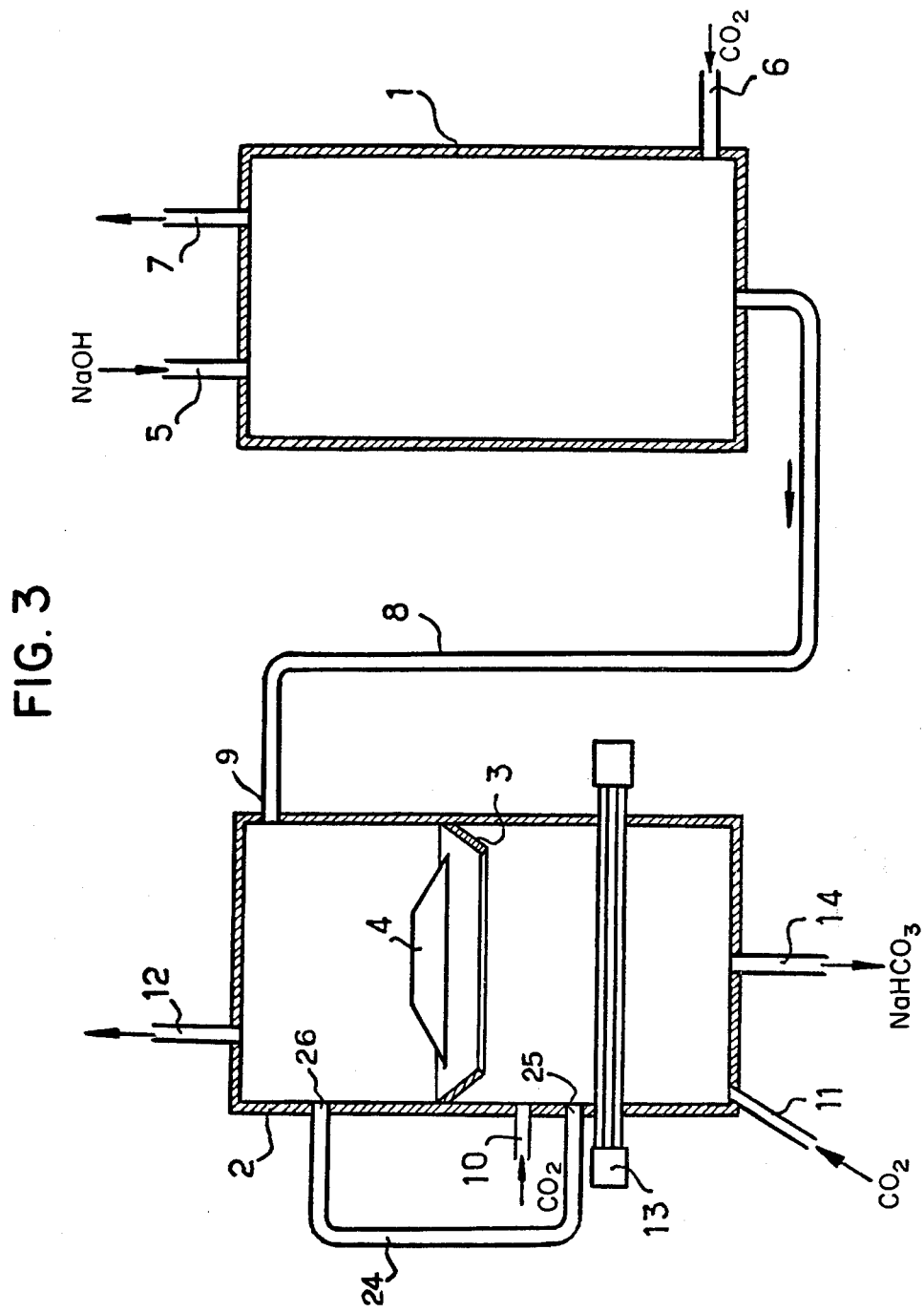

PROCESS FOR THE PRODUCTION OF SODIUM BICARBONATE FROM DIAPHRAM CELL LIQUORS

The present invention concerns a process of direct bicarbonation, in particular from effluents from electrolytic cells.

It also concerns the device for carrying out such a process, and the resulting product.

It has long been envisaged that sodium bicarbonate might be obtained from effluents from electrolytic cells.

Thus, U.S. Pat. No. 552,955 proposes feeding the cathodic compartment with an aqueous solution of sodium bicarbonate, feeding the anodic compartment with salt in solution, and decomposing it electrolytically, transferring the product from the cathodic compartment, after its conversion into monocarbonate, into a separate container, then treating it therein with carbon dioxide in a proportion such that the sodium carbonate solution is converted into sodium bicarbonate, then returning the solution to the cathodic compartment and forming a precipitate of sodium bicarbonate in a separate container, while maintaining a constant circulation of the liquid through the cathodic compartment and said container, with continuous electrolysis of the salt, and treating it with carbon dioxide, then recovering the precipitate from the liquid.

Since then, other processes have been proposed for producing bicarbonate in electrolytic cells.

However, the fact of operating in such cells suffers from disadvantages, in particular the disadvantage of the risk of interfering with operation of the electrolyzer, notwithstanding the substantial improvements made in the processes of the type described.

It was therefore thought that it would be more advantageous to separate the two operations, as disclosed in U.S. Pat. No. 2,383,674. In this patent, an unsaturated solution containing sodium hydroxide and sodium chloride from the cathodic compartment of an electrolytic cell, is treated by passing it through a sodium chloride bed, until saturation with respect to the sodium chloride and the sodium hydroxide; then the saturated solution is treated with carbon dioxide so as to convert as much as possible of the sodium hydroxide into bicarbonate, and finally filtering the resulting bicarbonate precipitate.

However, this process does not result in the desired control of the resulting product. Thus, in French Pat. No. 1,188,512, starting from the observation that the critical factors are alkalinity and the sodium chloride content of the mixture, the carbonation temperature, the speed of the gas flow and its carbon dioxide concentration, there is claimed a process which is characterized in that a carbonation operation is carried out on a solution of sodium carbonate containing sodium chloride, by contacting a sodium carbonate solution having an equivalent alkalinity of from 9.5% to 11.25% by weight of sodium carbonate and containing from 11.0% to 14.5% of sodium chloride, with a gas flow containing from 10% to 90% by volume of carbon dioxide at a flow rate of from 12 to 240 cm³ per minute to 100 cm³ of solution at a temperature of from 45° C to 100° C.

However, this process suffers from the disadvantage of being strictly dependent on the initial conditions in respect of concentration of the different reagents, and because of this does not permit treatment of effluent solutions as such.

Moreover, this process makes it necessary to treat the reagents, in a range for promotion of the reaction, at a given temperature in a reaction vessel in a discontinuous mode, and because of the concentrations required, necessitates the addition of sodium chloride in order to obtain an acceptable soda recovery yield, in bicarbonate form.

The applicants have found that the practical use of a direct bicarbonation process encountered difficulties derived in particular from the kinetics of the reactions involved. There are in fact the following three reactions:

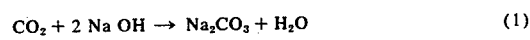

$$CO_2 + 2\,NaOH \rightarrow Na_2CO_3 + H_2O \qquad (1)$$

$$CO_2 + Na_2CO_3 + H_2O \rightarrow \text{dissolved } 2\,NaHCO \qquad (2)$$

$$\text{dissolved } NaHCO_3 \rightarrow \text{precipitated } NaHCO_3 \qquad (3)$$

The first reaction is rapid and is virtually complete, whereas the speed of the two other reactions is slow.

It is noted in particular that if operation is carried out in a reaction vessel at low temperature, the residence time for achieving equilibrium is substantial, and generally there is obtained a mixture of bicarbonate and carbonate, the crystals collected being of small size and difficult to decant, drain, wash and separate.

The result of this is that the sodium hydroxide yield recovered in this operation is greatly affected.

If, on the other hand, operation is at high temperature, a crusting phenomenon occurs which causes the reaction vessel to become blocked.

Moreover, for reasons of an economic nature, operation must be under conditions such as to arrive at a previously determined result, with a high yield of a marketable product, which makes it necessary to adopt a process which can be operated virtually continuously.

It has been found that these conditions can be fulfilled by employing the process which is the subject of the present invention and which comprises obtaining sodium bicarbonate by treating, in particular, effluent from an electrolytic cell, by the action of carbon dioxide, the process being characterized in that:

the sodium hydroxide contained in said effluent is converted into normal sodium carbonate, the carbonate thus formed is introduced into a sodium bicarbonate formation and precipitation zone, said zone being a gas-liquid exchange and solid-discharge zone, the products resulting from the second zone are finally introduced into an end-of-bicarbonation and cooling zone, said zone also being a gas-liquid exchange and solid-discharge zone in which the temperature is advantageously less than or equal to 45° C at the outlet from said zone.

The expression end-of-bicarbonation and cooling zone is intended to mean a zone in which the formation and precipitation of the bicarbonate is continued.

As already stated above, the effluent treated can be a solution coming directly from an electrolytic cell.

Preferably, such a solution contains from 160 to 210 g/liter of sodium chloride, and from 100 to 200 g/liter of sodium hydroxide.

Preferably, the gases used for reactions 2 and 3 contain at least 35% by volume of carbon dioxide, which makes it possible to operate with apparatus venting into atmosphere, but it would not be a departure from the scope of the present invention to operate under pressure, so as to use gases with a smaller content of carbon dioxide.

In addition, the maximum temperature attained in the second zone is advantageously below 70° C.

However, it has been surprisingly discovered that this temperature could be lowered by effecting recycling of a part of the suspension taken off from at least one point of the end-of-bicarbonation and cooling zone, introduced to at least one point located upstream of the point of maximum temperature. Optionally, it is also possible to effect recycling of the mother liquors. Advantageously, a part of the suspension taken off at the head of the end-of-bicarbonation and cooling zone is recycled to the head of the sodium bicarbonate formation and precipitation zone.

It has been noted in particular that, by virtue of this recycling of the suspension, it becomes possible to use the process with excellent results, with a low maximum temperature attained in the second zone, that is advantageously from 40° to 60° C.

It has been surprisingly observed that all conditions otherwise being equal, the product obtained had a higher mean diameter of crystals, as read on the screening curve.

The process according to the present invention can be carried out in an apparatus which is part of the invention and which is characterized in that it comprises, in combination:

in a first part, means for gas-liquid contact;

in a second part means for gas-liquid contact and solid discharge;

in a third part means for gas-liquid contact and solid discharge, associated with cooling means.

The gas-liquid contact means can comprise any known means such as a filled column, reaction vessels provided with agitator means, etc.

The gas-liquid contact and solid-discharge means can comprise an immersed column such as a column provided with small strainers or elements of gas syphon type such as those comprising an internal collar concentric with an external collar, the collars being disposed between two diaphragms, or by any equivalent means such as a bubble cap tower.

Finally, the cooling means simply comprise cooling devices such as liquid circulation coils.

The various means arranged as stated above can be distributed in a single device or in a plurality of devices. Preferably, however, the apparatus comprises at least two separate devices of which one contains gas-liquid contact means and the others each contain firstly gas-liquid contact and solid-discharge means and then gas-liquid contact and solid-discharge means associated with cooling means.

In a practical construction, said devices comprise immersed columns. It is of advantage for the gas-liquid contact means of the first column to be identical to the gas-liquid contact and solid-discharge means of the second column. In this way, the first column can operate in the washing mode, the bicarbonate that is deposited in an encrusting form being dissolved, while the other column or columns can operate in the reaction mode.

In addition, the apparatus according to the present invention can comprise means for recycling a part of the suspension taken off at at least one point of the end-of bicarbonation and cooling zone, to at least one point disposed upstream of the point of maximum temperature. Such an apparatus can comprise in addition other recycling means, in particular for the mother liquors.

The present invention, however, will be more readily understood by reference to the following examples:

EXAMPLE 1

Use is made of an apparatus as diagrammatically shown in FIG. 1 which comprises an immersed column 1 operating in the washing mode and an immersed column 2 operating in the reaction mode.

These two columns have an internal structure comprising gas-liquid contact and solid-discharge means comprising strainer elements such as that shown in the diagrammatic view of column 2, which comprises a collar 3 surmounted by a bell member 4.

The initial lye is introduced into the column 1 by way of an inlet conduit 5, the gas containing carbon dioxide is introduced in a conduit 6 into the column 1, and the surplus of carbon dioxide and the inert gases are discharged by way of a conduit 7.

The lye resulting from the passage through the column 1 then passes by way of a conduit 8 into the column 2 into which it is introduced at the head. Carbon dioxide is introduced into the column 2 to 10 and 11, the surplus of carbon dioxide and the inert gases being discharged at 12. In its lower portion, the column 2 has cooling means comprising a cooling coil 13 and a conduit 14 for discharge of the suspension.

With an apparatus comprising two columns having an internal diameter of 1.80 m and a height of 20 m, a lye having the following composition is introduced:

Na Cl: 190 g/l
Na CH: 120 g/l at a flow rate of 15 m³/hour, and this lye is treated by means of a gas containing by volume 40% of carbon dioxide.

A third of the total amount of carbon dioxide is introduced respectively at 6, 10 and 11. The inlet temperature of the carbon dioxide is 28° C. The maximum temperature reached in the sodium bicarbonate precipitation zone is equal to 58° C.

The temperature of the slurry collected at the base of the second column is 25° C.

The yield in respect of recovery of soda in bicarbonate form is 89.9%.

The slurry collected is a suspension of bicarbonate, decantered and easily filtered, free from sodium chloride and sodium carbonate. The crystals collected have a mean diameter of 180 $\mu$, as read on a screening curve.

EXAMPLE 2

Figure 2:
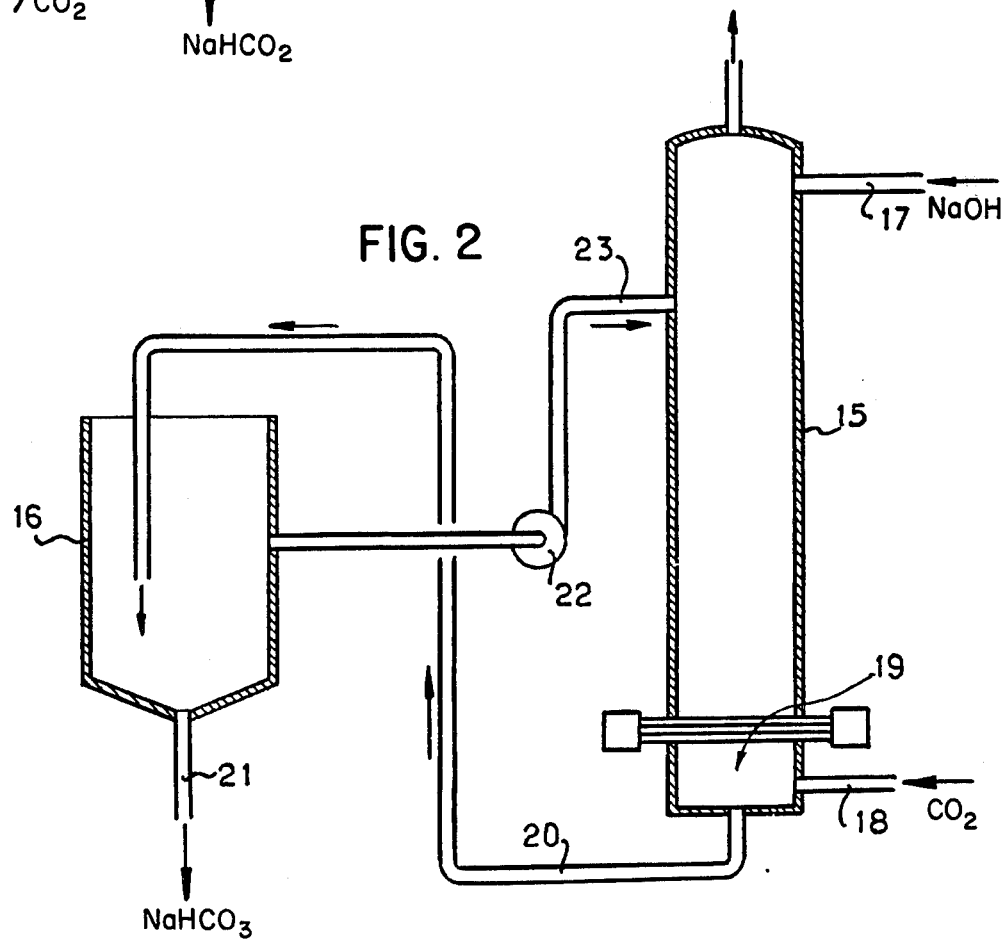

An apparatus is used such as that diagrammatically shown in FIG. 2, comprising an immersed column 15 operating in the reaction mode and a continuous decanter 16.

The column 15 is provided with strainer members. It is 150 mm in diameter and 9 m in height. The decanter 16 has a capacity of 50 liters. The effluent is introduced at 17 at a flow rate of 50 liters/hour and comprises a lye originating from electrolysis and comprising 126 g/l of NaOH and 183 g/l of NaCl.

The carbonation gas is introduced at 18 at the base of the column 15, and contains 68% by volume $CO_2$. The maximum temperature reached in the precipitation zone is about 55° C.

The slurry issues from the cooling zone 19 at a temperature of 45° C, and is then discharged by way of a conduit 20 to the decanter 16.

The crystals of bicarbonate formed are collected at the base of the decanter at 21, while a pump 22 provides for recycling of clear liquid at 23, to the head of the precipitation zone at a flow rate of 50 l/h.

It is noted that the conversion of soda into bicarbonate is total, and the precipitation yield is 84%.

Moreover, the formed bicarbonate crystals decant easily and can be readily filtered and washed.

In this example, use was made of an effluent originating directly from an electrolysis operation, but obviously, as in the preceding example, it is possible to resort to a column operating in a washing mode.

EXAMPLE 3

In this example, use is made of an apparatus as illustrated in FIG. 3.

This apparatus is similar to that shown in FIG. 1, except that it comprises means for recycling the suspension taken off at at least one point of the end-of-bicarbonation and cooling zone, to at least one point located upstream of the point of maximum temperature, and comprising a recycling conduit 24 communicating with the interior of the column 2 by way of two apertures 25 and 26.

With an apparatus comprising two columns having an internal diameter of 1.80 m and a height of 20 m, a lye having the following composition is introduced:

NaCl: 192 g/l
NaOH: 112 g/l with a flow rate of lye of 14 m³/hour, and this lye is treated with:

a gas which contains by volume 40% of carbon dioxide and which is introduced at 6 in an amount such that the concentration of sodium hydroxide in the conduit 8 is equal to 22 g/liter, and a gas containing by volume 80% of carbon dioxide, introduced at 11.

In each case, the gas inlet temperature is 30° C.

In addition, there is recycling, at a flow rate of 30 m³/h, of some suspension taken off at 25, at the head of the end-of-bicarbonation and cooling zone, and returned to the column at 26 at the head of the sodium bicarbonate formation and precipitation zone.

The maximum temperature reached in the sodium bicarbonate formation and precipitation zone is 48° C. The temperature of the slurry collected at the base of the second column is 30° C. The yield in respect of recovery of soda in bicarbonate form in 88.4%.

The slurry collected is a suspension of bicarbonate that is decanted and filtered easily, being free from sodium chloride and sodium carbonate. The crystals collected have a mean diameter of 100 $\mu$, as read on a screening curve.

The cycle is 3 continuous days without blockage, and with a high level of operating flexibility, whereas the same operation without recycling has a cycle time of the order of 2 days and involves a maximum temperature of 58° C for the same flow rate.

EXAMPLE 4

In this example, use is made of the same apparatus as that of Example 3, and two comparative tests are carried out, one with and the other without recycling.

The operating conditions are as follows:
lye composition NaCl 200 g/l
NaOH 104 g/l
flow rate of the lye: 10 m³/h
gas: gas is introduced that contains by volume 40% of carbon dioxide, in equal parts, at 6, 10 and 11, at a temperature of 30° C.

The maximum temperature reached in the sodium bicarbonate formation and precipitation zone is equal to 51° C.

The temperature of the slurry collected at the base of the second column is 30° C.

The yield, in respect of recovery of soda in bicarbonate form, is 88.2%.

It is noted that if operation is carried out with recycling, the bicarbonate crystals collected are of a mean diameter of 170 $\mu$, whereas if the operation is effected without recycling, the mean diameter of the crystals is only 155 $\mu$.

This example therefore reveals the unexpected effect on the size of the crystals, resulting from carrying out the process according to the invention.

We claim:

1. A continuous method for obtaining sodium bicarbonate as crystals of a size to enable easy separation by filtration by the treatment with $CO_2$ of sodium chloride electrolysis diaphragm cell liquor containing sodium hydroxide and sodium chloride, comprising:

in a first zone treating the cell liquor with a carbon dioxide containing gas in an amount to convert sodium hydroxide to a neutral sodium carbonate which remains in solution;

in a second zone subjecting the solution from the first zone to the action of a carbon dioxide containing gas to precipitate a portion of the sodium carbonate as sodium bicarbonate while maintaining the maximum temperature in said second zone below 70° C;

passing the suspension obtained from the second zone to a third zone whereby bicarbonation is completed by the action of a carbon dioxide containing gas, and cooling the suspension to a final temperature of no more than 45° C; and finally separating the precipitated sodium bicarbonate, which includes the step of recycling a part of the suspension from the third zone back into the second zone.

2. A process as claimed in claim 1 in which the maximum temperature reached in the second zone is from 40° to 60° C.

3. A process as claimed in claim 1 in which the electrolysis liquor contains from 160 to 210 g/l of sodium chloride and from 100 to 200 g/l of sodium hydroxide.

4. A process as claimed in claim 3, in which the electrolysis liquor is treated by a gas containing at least by volume 35% of carbon dioxide.

5. A process as claimed in claim 4 in which the carbon dioxide containing gas is under pressure.

6. A continuous method for obtaining sodium bicarbonate as crystals of a size to enable easy separation by filtration by the treatment with $CO_2$ of sodium chloride electrolysis diaphragm cell liquor containing sodium hydroxide and sodium chloride, comprising:

in a first zone treating the cell liquor with a carbon dioxide containing gas in an amount to convert sodium hydroxide to a neutral carbonate which remains in solution;

in a second zone subjecting the solution from the first zone to the action of a carbon dioxide containing gas to precipitate a portion of the sodium carbonate as sodium bicarbonate while maintaining the maximum temperature in said second size below 70° C;

passing the suspension obtained from the second zone to a third zone whereby bicarbonation is completed by the action of a carbon dioxide containing gas, and cooling the suspension to a final temperature of no more than 45° C; and finally separating the precipitated sodium bicarbonate which includes the step in which a portion of the suspension from the third zone is recycled to the head of the second zone.

7. A continuous method for obtaining sodium bicarbonate as crystals of a size to enable easy separation by filtration by the treatment with $CO_2$ of sodium chloride electrolysis diaphragm cell liquor containing sodium hydroxide and sodium chloride, comprising:

in a first zone treating the cell liquor with a carbon dioxide containing gas in an amount to convert sodium hydroxide to a neutral sodium carbonate which remains in solution;

in a second zone subjecting the solution from the first zone to the action of a carbon dioxide containing gas to precipitate a portion of the sodium carbonate as sodium bicarbonate while maintaining the maximum temperature in said second zone below 70° C;

passing the suspension obtained from the second zone to a third zone whereby bicarbonation is completed by the action of a carbon dioxide containing gas, and cooling the suspension to a final temperature of no more than 45° C; and finally separating the precipitated sodium bicarbonate, which includes the step of recycling mother liquor resulting from the separation of the sodium bicarbonate from the effluent of the third zone to the head end portion of the second zone.

8. A continuous method for obtaining sodium bicarbonate as crystals of a size to enable easy separation by filtration by the treatment with $CO_2$ of sodium chloride electrolysis diaphragm cell liquor containing sodium hydroxide and sodium chloride, comprising:

in a first zone treating the cell liquor with a carbon dioxide containing gas in an amount to convert sodium hydroxide to a neutral sodium carbonate which remains in solution;

in a second zone subjecting the solution from the first zone to the action of a carbon dioxide containing gas to precipitate a portion of the sodium carbonate as sodium bicarbonate while maintaining the maximum temperature in said second zone below 70° C;

passing the suspension obtained from the second zone to a third zone whereby bicarbonation is completed by the action of a carbon dioxide containing gas, and cooling the suspension to a final temperature of no more than 45° C; and finally separating the precipitated sodium bicarbonate, which includes the step of recycling part of the suspension from the head of the third zone to the head of the second zone.

* * * * *

UNITED STATES PATENT OFFICE
CERTIFICATE OF CORRECTION

Patent No. 4,032,616          Dated June 28, 1977

Inventor(s) Andre Artur and Charles Meniere

It is certified that error appears in the above-identified patent and that said Letters Patent are hereby corrected as shown below:

column 6, line 67, after "neutral" add -- sodium -- .

Signed and Sealed this

Twentieth Day of September 1977

[SEAL]

Attest:

RUTH C. MASON  
Attesting Officer

LUTRELLE F. PARKER  
Acting Commissioner of Patents and Trademarks